United States Patent [19]

Frilette et al.

[11] 4,157,950
[45] * Jun. 12, 1979

[54] CONVERSION OF HYDROCARBONS

[75] Inventors: Vincent J. Frilette, Morrisville; Mae K. Rubin, Bala Cynwyd, both of Pa.

[73] Assignee: Mobil Oil Corporation, New York, N.Y.

[*] Notice: The portion of the term of this patent subsequent to Apr. 18, 1995, has been disclaimed.

[21] Appl. No.: 842,833

[22] Filed: Oct. 17, 1977

Related U.S. Application Data

[63] Continuation of Ser. No. 165,702, Jul. 23, 1971, Pat. No. 4,085,156, which is a continuation-in-part of Ser. No. 697,610, Aug. 3, 1971, Pat. No. 3,597,493, which is a continuation of Ser. No. 494,228, Oct. 8, 1965, abandoned, which is a continuation of Ser. No. 142,778, Oct. 4, 1961, abandoned.

[51] Int. Cl.$^2$ .................. C10G 35/06; C07C 3/52
[52] U.S. Cl. .................. 208/135; 208/120; 585/374; 585/407; 585/467; 585/475; 585/476; 585/752
[58] Field of Search .................. 208/120, 135; 260/671 C, 671 R, 673

[56] References Cited

U.S. PATENT DOCUMENTS

| | | | |
|---|---|---|---|
| 2,904,607 | 8/1959 | Mattox et al. | 260/671 C |
| 3,033,778 | 5/1962 | Frilette | 208/120 |
| 3,039,953 | 6/1962 | Eng | 208/26 |
| 3,114,696 | 12/1963 | Weisz | 208/66 |
| 3,140,253 | 7/1974 | Plank et al. | 208/120 |

*Primary Examiner*—C. Davis
*Attorney, Agent, or Firm*—Charles A. Huggett; Raymond W. Barclay

[57] ABSTRACT

Crystalline aluminosilicate zeolites are used as catalysts for various hydrocarbon conversion processes and are particularly useful for conversion of paraffins in the presence of an alkylatable aromatic hydrocarbon such as benzene.

9 Claims, No Drawings

CONVERSION OF HYDROCARBONS

CROSS REFERENCES TO RELATED APPLICATIONS

This application is a continuation of Ser. No. 165,702 filed July 23, 1971, now U.S. Pat. No. 4,085,156 which is a continuation-in-part of application Ser. No. 697,610, filed Aug. 3, 1971, now U.S. Pat. No. 3,597,493, issued Aug. 3, 1971, which in turn is a continuation of application Ser. No. 494,228, filed Oct. 8, 1965 now abandoned, which in turn, is a continuation of application Ser. No. 142,778, filed Oct. 4, 1961, now abandoned.

DESCRIPTION OF THE PRIOR ART

The conversion of paraffins in the presence of an aklylatable aromatic hydrocarbon is a known reaction which has been heretofore carried out in the presence of amorphous silica alumina at temperatures of 550°–660° C. (Mamadaliev, Yu. G., and Bakhshi - Zade, A. A., Dokl. Akad, Nauk. Azerb. S. S. R. 12,819 (1956); Chem. Abstr. 51, 7317 (1957).

DESCRIPTION OF INVENTION

This invention has to do with the catalytic conversion of hydrocarbons and is particularly concerned with carrying out such conversions over a catalytic material of unique capabilities.

Zeolitic materials, both natural and synthetic, in naturally occurring and modified forms have been demonstrated as having catalytic capabilities for hydrocarbon conversion. Such zeolitic materials are ordered crystalline aluminosilicates having definite crystalline structure within which there are passages, pores, or cavities of definite ranges of size. Since the dimensions of these pores are such as to accept for adsorption molecules or certain dimensions while rejecting those of larger dimension, these materials have been referred to as "molecular sieves" and utilized in many ways taking advantage of these properties.

A newly investigated zeolitic material is mordenite. Mordenite is an ordered crystalline alumino-silicate, having a ratio of silicon atoms to aluminum atoms of about 5 to 1. It occurs naturally and has also been synthesized. It occurs usually as the sodium salt and corresponds to the formula:

$$Na_8(AlO_2)_8(SiO_2)_{40}24H_2O \quad 1$$

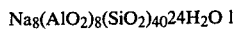

The ordered alumino-silicate crystalline framework of mordenite differs from that of other known zeolites in that it is composed of chains of 5-membered rings of tetrahedra and its porosity indicates one parallel system of channels having free diameters of the order of 4A to 6.6 A, interconnected by smaller channels, parallel to another axis of the order of 2.8 A free diameter.

This invention is specifically concerned with various conversions of hydrocarbons in the presence of activated mordenite and its applications to hydrocarbon conversion as its object. Other objects are in part obvious and in part appear hereinafter.

The unique catalyst with which this invention is concerned may be prepared by the activation of naturally occurring mordenite. One method of preparation is to reduce the material to a fine powder, at least passing the standard 200-mesh sieve, and preferably passing 300-mesh or 325-mesh standard sieves, or finer, followed by acid treatment. A specific example of acid treatment is to contact 10 grams of a powdered mordenite passing a 325-mesh sieve with 125 to 200 ml. of 0.1N HCl for 15 minutes, filter, and repeat, then treat with 125 to 200 ml. of 1.2N HCl for 15 minutes, and repeat (all at room temperature), followed by rinsing until filtrate shows no acidity. The filter cake, dried at 120° C. and pelleted, will yield about 8 grams of catalytic material.

Such treatment as above outlined will result in an activated mordenite at least 50% of which is in the "H" or acid form. Since the presence of alkaline earth metal ions in the ordered crystalline structure sometimes is found to confer a degree of stability, such materials may be present. If the naturally occurring mordenite contains calcium, as it frequently does, the acid treatment may be so handled as to leave a portion present, or the alkaline earth metal ions may be introduced by base exchange in known manner. However, the amount of calcium or similar substitution should be carefully controlled and held to values such as do not materially alter the conversion capabilities of the catalyst which should be at least 50% in the acid or "H" form.

Also, the material may be treated in known manner to incorporate certain active trivalent metals, such as cerium, lanthanum, iron, and the like, capable of modification of the catalytic reactions.

Similarly, the proportion of aluminum, in the trivalent form, may be increased, with significant alteration in the catalytic activity of the material for many reactions.

Such a catalyst is capable of adsorbing carbon dioxide to the extent of about 10% of its own weight. It is further and most strikingly characterized by a capability of converting normal hexane to the extent of about 20 weight percent at a temperature of 240° C. (465° E.) and a partial pressure of about 150 mm. in the presence of an inert gas, at a liquid hourly space velocity of about 0.5 in a ten-minute duration run in fixed bed operation.

To further characterize this catalytic material, it has a surface area in the "H" form of 300 m²/gm and above.

It is thermally stable upon repeated exposure (e.g. regenerations) to temperatures of the order of 600° C. (1,110° F.) and even up to about 800° C. (1470° F.) under certain conditions.

Summarizing these properties, when the term "catalyst of the acid-activated mordenite type" is used hereinafter, that term refers to a material:

1. Having an atomic ratio Si/Al of about 5/1.
2. Having the crystalline structure of mordenite as shown by powder X-ray diffraction.
3. Having the acid or "H" form, or not more than about 50% as a partial salt thereof.
4. Having a surface area of at least 300 $M^2$/gm.
5. Thermally stable.
6. Capable of converting hexane to the extent of about 20 weight percent at a temperature of 240° C. and a partial pressure of about 150 mm. in the presence of an inert gas, at a liquid hourly space velocity of about 0.5 in a run of ten minutes duration in a bed operation.

HYDROCARBON CRACKING

As an example of the high and unexpected capability of this catalyst of the acid-activated mordenite type, reference is made to the conversion of normal hexane. In the presence of a conventional type of silica-alumina catalyst, amorphous in nature, of an activity index of 46, hexane is stable until temperatures of the order of 500° C. (930°F.) are reached.

In contrast, when passed in contact with the present catalyst, hexane undergoes substantial conversion at 240° C. (435° F.), in a low concentration in inert gas carrier.

While it is known that crystalline alumino-silicates are more active than the amorphous forms, the present catalyst is more active than the usual crystalline alumino-silicates. In contrast to the substantial conversion of hexane at 240° C. (435° F.) noted above for this catalyst, the "acid" form of the Y variety of faujasite does not exhibit conversion of hexane until temperatures of about 330° C. (625° F.) are reached.

A further notable characteristic of the conversion of paraffinic materials over this catalyst is the nature of the products of conversion. With hexane charge, there are no $C_4$ olefins or lower olefins produced, the effluent products being saturated, and a substantial portion of those products—from 40–60% of them—being isobutane and isopentane. Some isohexane also may be produced. Also notable is the fact that "dry" gas, that is, methane and ethane, is not produced in detectable quantities.

This conversion, in the production of iso-compounds, the absence of methane and ethane, the indicated ability for hydrogen transfer, resembles the conversion accomplished over catalysts of the type of $AlCl_3$ rather than those usually associated with silica-alumina catalysts.

At higher temperatures, the product distribution changes. With hexane charge, at about 410° C. (770° F.), hexane is highly converted, and olefins, toluene, and benzene appear in the product. The appearance of aromatics indicates a reforming capability of this catalyst, and that at a temperature about 100° C. lower than those usually utilized for reforming over platinum catalysts.

Conversion of normal heptane over this catalyst behaves similarly, except that conversion sets in at the lower temperature of 180° C. (355° F.), and aromatic compounds appear in the products of conversion at temperatures of about 300° C. (575° F.), heptane being almost wholly converted at temperatures of about 320° C. (610° F.).

It will be realized from the above data that this catalyst presents a unique utility not only for the cracking of normal petroleum fractions, but for the "reforming" of naphthas of low anti-knock capability to produce products of higher anti-knock value. The "$C_6$ cut" of normally produced gasoline, composed mainly of hexane, but also containing significant quantities of pentane and heptane is ordinarily considered a somewhat difficult thing to handle in upgrading and in some cases resort is had to very high temperature thermal cracking to destroy it with the production of ethylene, propylene, and other fragments which then may be tailored into effective anti-knock components or diverted into profit channels other than gasoline.

With this present catalyst, this fraction can be converted to desirable product at relatively low temperatures.

For example, in a fixed bed operation conducted at temperatures of the order of 400°–420° C. (750°–800° F.), at a space velocity of the order of 0.5 (liquid volume charge at 20° C./volume occupied by catalyst, at a partial pressure of about 150 mm. in the presence of inert gas, and for a 10-minute duration of cracking portion of the cycle, in excess of 50% (weight %) of a material composed mainly of hexane will be converted to toluene, benzene, iso-compounds, and olefins suitable for alkylation.

The regeneration of this catalyst is readily accomplished with air at temperatures of 300° C. (575° F.), and upwards to about 600° C. (1110° F.).

Thus, the catalyst lends itself readily to any form of cyclic process in which it is alternately exposed to conversion of a charge and to regeneration.

CONVERSION OF CYCLOPARAFFINS

This catalyst of the acid-activated mordenite type is also quite active for the conversion of cycloparaffins, at relatively low temperatures and in the absence of a dehydrogenation component.

For example, in an extended experiment wherein cyclohexane feed, at a partial pressure of about 80 mm., (helium stream saturated with cyclohexane), at a liquid hourly space velocity of about 0.2, and at a temperature of 270° C. (518° F.), the following was observed.

TABLE I

| Minute on Stream | Conversion Products (wt. %) Methyl-Cyclopentane | During that Minute Other | Total |
|---|---|---|---|
| 22nd | 10.7 | 2.6 | 13.3 |
| 37th | 11.2 | 1.6 | 12.8 |
| 134th | 11.0 | 1.1 | 12.1 |
| 164th | 11.5 | 0.9 | 12.4 |

The continued conversion ability of the catalyst under these conditions is of considered significance.

In a similarly conducted experiment with methyl cyclohexane at increasing temperatures, the following was noted:

TABLE II

| Temp. °C. | Wt. % Methylcyclohexane Converted |
|---|---|
| 250° (482° F.) | 7.4 |
| 320° (608° F.) | 29.0 |
| 370° (680° F.) | 90.0 |

At the highest temperature, the products included dimethylcyclopentanes and aromatics.

BENZENE CONVERSION

It has been found that the catalytic conversion of benzene to other products such as toluene and ethylbenzene can be accomplished at reasonable temperature levels over this catalyst of acid-activated mordenite type.

This is somewhat unusual in that benzene would not normally be considered a compound which would undergo transformation over oxide catalysts. In the usual case, over amorphous catalytic materials composed of silica-alumina complexes, benzene appears to be a relatively quite stable product, as, for example, in the cracking of petroleum hydrocarbons.

Nevertheless, with the present catalyst, the production of alkylaromatics begins with the appearance of toluene in the products of treatment at about 375° C. (689° F.) with ethyl benzene appearing at about 450° C. (846° F.), and in increasing amounts as the temperature is increased, until, in passing over a fixed bed of this catalytic material at a temperature of about 525° C. (977° F.), about 16 weight percent of the benzene fed appears as toluene and ethylbenzene.

ALKYLATION OF BENZENE

Alkylation of benzene may be conducted over this catalyst of acid-activated mordenite type at relatively conservative temperature levels, and in vapor phase or liquid phase as appropriate for the temperature conditions used.

For example, in vapor phase, ethylene and benzene may be passed together, with benzene in excess, to produce ethyl benzenes and other alkyl benzenes. With about 2/1 mol proportions of benzene and ethylene, ethyl benzene is produced at about 100° C. and appears in significant quantities beginning at about 150° C. (300° F.) at atmospheric pressure. The amount of benzene converted to alkyl benzenes follows a temperature pattern in accordance with the following:

TABLE III

| Temp. °C. | Wt. % Benzene Converted |
|---|---|
| 152° | 4.2 |
| 162° | 4.2 |
| 240° | 6.2 |
| 383° (721° F.) | 14.6 |

In addition to ethyl benzene, and particularly at the higher temperatures, the effluent was found to contain diethyl benzene, o-xylene, cumene, and some toluene.

The above experiments were carried out with a stream of helium as carrier gas, saturated with benzene at atmospheric temperature and pressure, to which the desired amount of ethylene had been added.

Similarly, but in liquid phase, alkylation of benzene with propylene is found to proceed readily in liquid phase at temperatures of about 78° C. (175° F.) with the production of cumene. Benzene was provided in excess. The catalyst used was the dried powder form, slurried into the reaction mixture, this mixture being gotten by flowing propylene in vapor form into a body of benzene. The rate of production of cumene was found to be about 0.84 mols cumene/hour/gram of catalyst at 78° C.

TOLUENE DISPROPORTIONATION

This catalyst of the acid-activated mordenite type exhibits a high capability for the disproportionation of toluene, as shown by the following data:

TABLE IV

| Disproportionation of Toluene at 300° C. (572° F.) | |
|---|---|
| Minute on Stream | Conversion During that Period, Wt. % |
| 24–27, incl. | 47.3 |
| 62–68, incl. | 46.4 |
| 73–77, incl. | 38.6 |
| 91st | 33.0 |
| 120th | 30.0 |
| 170th | 24.3 |

The liquid hourly space velocity of this operation was about 0.04, at a toluene partial pressure of about 20 mm. in a stream of helium carrier gas. The products were mainly xylenes and benzene, and no evidence of light fragments was detected.

In contrast, passing toluene over an amorphous silica-alumina catalyst of 46 Activity Index, only about 2% conversion can be had at 546° C. (1013° F.).

INTERCEPTION OF CRACKING BY ALKYLATION

It was noted earlier in this specification that, while the cracking of paraffins at lower temperatures over this catalyst of acid-activated mordenite type did not give rise to olefins, at higher temperatures, olefins were formed. It has also been noted that alkylation of benzene with olefins is possible at relatively low temperatures over this catalyst.

This combination of capabilities gives rise to an interesting conversion, wherein a paraffin, such as heptane is cracked over this catalyst at conversion temperatures in the presence of an alkylatable material such as benzene.

The course of such treatment with temperature is shown by the following:

TABLE V

| N-Heptane Cracking in Presence of Benzene | | | |
|---|---|---|---|
| Temp. C. | Benzene Conv. Wt. % | Heptane Conv. Wt. % | |
| 130° | 0 | 7 | Cracked Products |
| 172° | 0 | 21 | Cracked Products |
| 275° | 3.6 | 47 | Cracked Products |
| 331° | 6.1 | 92 | Cracked Products plus toluene, ethyl benzene, xylene |
| 360 (680° F.) | 21.0 | 95 | Cracked Products plus toluene, xylene, diethylbenzene |

Other representative crystalline aluminosilicate zeolites which can be used in the conversion of paraffins in the presence of an alkylatable material include zeolite Beta, TEA mordenite, ZSM-12, TMA offretite, ZSM-4, and preferably have a silica to alumina ratio of at least 10.

Zeolite Beta is a well known zeolite synthesized from a solution containing tetraethylammonium ions and is described and claimed in U.S. Pat. No. 3,308,069.

TEA mordenite is also synthesized from a solution containing tetraethylammonium ions and has the following formula in terms of mole ratios of oxides in its synthesized form:

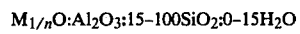
$$M_{1/n}O:Al_2O_3:15-100SiO_2:0-15H_2O$$

wherein M is a mixture of cations, at least one of which is tetraalkylammonium and n is the valence of M.

TEA mordenite has the crystal structure of mordenite.

TEA mordenite is disclosed and claimed in copending application Ser. No. 795,694, filed Jan. 31, 1969.

ZSM-12 as synthesized has a formula in terms of mole ratios of oxides as follows:

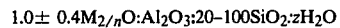
$$1.0\pm 0.4M_{2/n}O:Al_2O_3:20-100SiO_2:zH_2O$$

TMA offretite is a crystalline aluminosilicate having a definite crystal structure similar to natural offretite and containing tetramethylammonium ions. It is prepared from a mixture of silica, alumina, water, sodium oxide, potassium oxide and tetramethylammonium oxide and in its synthesized form has the following formula:

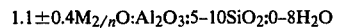
$$1.1\pm 0.4M_{2/n}O:Al_2O_3:5-10SiO_2:0-8H_2O$$

wherein M is a mixture of cations, at least one of which is tetramethylammonium and one is the valence of M.

TMA offretite is disclosed in copending application Ser. No. 59,340, filed July 29, 1970.

ZSM-4 is disclosed in U.S. Pat. No. 3,578,723.

In the following examples, equal parts by weight of benzene and n-heptane were charged over various crystalline aluminosilicates and the conversion of benzene and heptane was measured. The results are shown below in Table VI.

The conditions employed were as follows:

| Temperature | 600°–900° F. |
|---|---|
| Pressure | 0–400 psig |
| WHSV | 0.4–62 |
| $H_2/HC$ | 0–7 |

TABLE VI

| Zeolite | $SiO_2/Al_2O_3$ | n-heptane Cracked Wt. % | Benzene Converted Wt. % | Temp., F. |
|---|---|---|---|---|
| TMA offretite | 8.0 | 15 | 1.5 | 800 |
| ZSM-4 | 6.7 | 8 | 0.1 | 750 |
| Mordenite (Dealuminized) | 24 | 9 | 2 | 750 |
| TEA Mordenite | 32 | 61 | 18.5 | 900 |
| Beta | 30 | 68 | 10.5 | 900 |
| ZSM-12 | 52 | 52 | 18 | 750 |

The crystalline aluminosilicate zeolites which are used preferably have the original cations associated therewith replaced by a wide variety of other cations according to techniques well known in the art. Typical replacing cations would include hydrogen, ammonium and metal cations, including mixtures of the same. Of the replacing cations, particular preference is given to cations of hydrogen, ammonium, rare earth, magnesium, zinc, calcium, nickel, and mixtures thereof.

Typical ion exchange techniques would be to contact the particular zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the zeolites may be washed with water and dried at a temperature ranging from 150° F. to about 600° F. and thereafter heated in air or other inert gas at temperatures ranging from about 500° F. to 1500° F. for periods of time ranging from 1 to 48 hours or more.

It is also possible to treat the zeolite with steam at elevated temperatures ranging from 800° F. to 1600° F. and preferably 1000° F. and 1500° F., if such is desired. The treatment may be accomplished in atmospheres consisting partially or entirely of steam.

A similar treatment can be accomplished at lower temperatures and elevated pressures, e.g. 350°–700° F. at 10 to about 200 atmospheres.

A preferred embodiment of this invention resides in the use of a porous matrix together with the zeolites previously described. The zeolites can be combined, dispersed or otherwise intimately admixed with a porous matrix in such proportions that the resulting product contains from 1% to 95% by weight, and preferably from 10 to 80% by weight of the zeolite in the final composite.

The term "porous matrix" includes inorganic compositions with which the aluminosilicates can be combined, dispersed or otherwise intimately admixed wherein the matrix may be active or inactive. It is to be understood that the porosity of the compositions employed as a matrix can either be inherent in the particular material or it can be introduced by mechanical or chemical means. Representative matrices which can be employed include metals and alloys thereof, sintered metals and sintered glass, asbestos, silicon carbide aggregates, pumice, firebrick, diatomaceous earths, alumina, and inorganic oxides. Inorganic compositions especially those of a siliceous nature are preferred. Of these matrices, inorganic oxides such as clay, chemically treated clay, silica, silica-alumina, etc., are particularly preferred because of their superior porosity, attrition resistance, and stability.

Techniques for incorporating the zeolites in a matrix are conventional in the art and are set forth in U.S. Pat. No. 3,140,253.

While the foregoing examples have illustrated n-heptane cracking in the presence of benzene, such reaction is merely representative and a wide variety of feed materials can be employed, including normal and slightly branched chain paraffins with various alkylatable mono-and polynuclear aromatic hydrocarbons which have an open (non-substituted) para-position such as benzene, toluene, ethylbenzene, cumene, t-butyl benzene and the like.

Particularly suitable feed materials are reformates or reformer effluents composed of substantially aromatic and paraffinic constituents. Such materials are conventionally obtained by reforming a naphtha fraction having an initial boiling point within the range of about 140° F. to about 350° F. and an end boiling point in the range of about 250° F. to 425° F. to yield a reformate containing normal paraffins, iso-paraffins and cyclic hydrocarbon components.

The reforming operation is carried out under the conventional conditions of reforming employed in the art. Such conditions involve the use of a temperature between about 800° F. and 1000° F. and usually a temperature between about 850° F. and 975° F. The pressure during reforming is generally within the range of about 100 to about 1000 pounds per square inch gauge and more usually between about 200 and about 700 pounds per square inch gauge. The liquid hourly space velocity employed, i.e., the liquid volume of hydrocarbon per hour per volume of catalyst is between about 0.1 and about 10 and usually between 0.5 and 4. In general, the molar ratio of hydrogen to hydrocarbon charge employed is between about 1 and about 20 and preferably between about 4 and about 12. The catalysts employed in the reforming step may be any of those conventionally used, including, for example, the oxides of group VI metals such as molybdenum, or chromium, a metal of the platinum series such as platinum, palladium, osmium, iridium, ruthenium, or rhodium deposited on a suitable support such as silica, alumina, or components thereof.

A typical reformate $C_6+$ boiling range fraction has the following composition:

|  | Weight per cent |
| --- | --- |
| N-Hexane | 27.1 |
| 2-methyl pentane | 26.7 |
| 3-methyl pentane | 18.9 |
| 2,2 di-methyl butane | 3.7 |
| 2,3 di-methyl butane | 5.2 |
| Cyclic compounds | 12.3 |

The material in this boiling range, by virtue of its limited content in multiple branching and the remaining high concentration of normal paraffin has a relatively low octane rating. Because of the highly depressing blending octane value of such normal paraffins as n-hexane, it has heretofore been suggested to separate the same from the reformate product and either to discard them or to reprocess them in a separate system. However, by means of cracking paraffins in the presence of an alkylatable material a portion of the aromatic rings of the feed are simultaneously alkylated with products resulting from the cracking of normal and/or slightly branched paraffins, thereby resulting in higher alkylated aromatic rings in the product. Thus, undesirable materials are removed and used to form alkyl aromatics, thereby enhancing the quality of a reformate.

In accordance with this embodiment, the reformate or reformer effluent is contacted with or without added hydrogen over a crystalline aluminosilicate catalyst, preferably one which has a silica to alumina ratio of at least 10. The process chemistry seems the same with or without the presence of hydrogen. Although there does not appear to be any chemical reason that makes hydrogen necessary in order to upgrade the reformate, from a practical point of view it appears that the production of the reformate via a reforming reaction always results in the production of hydrogen and it would neither be necessary nor desirable to separate out this hydrogen which, in fact, may provide added benefits insofar as the catalyst is concerned, particularly with respect to stability. Practically, it is undesirable to separate out the hydrogen because it would add to processing cost. It is to be understood, however, that it is not necessary to have a hydrogenation/dehydrogenation component associated with the catalyst. Thus, this embodiment includes processing of a reformate or reformer effluent either in the absence or in the presence of hydrogen over the zeolite catalysts previously described with or without an added hydrogenation component.

The cracking of paraffins in the presence of an alkylatable aromatic is generally carried out at a temperature between 500° F. and about 1000° F. and preferably 550°–850° F. The hydrogen pressure, if such is used, in such operation is generally within the range of about 100 and about 3000 psig and preferably about 350 to about 2000 psig. The liquid hourly space velocity, i.e., the liquid volume of hydrocarbon per hour per volume of catalyst is about 0.1 and about 250, and preferably between about 1 and 100. In general the molar ratio of hydrogen to hydrocarbon charge employed is between about 1 and about 80, and preferably between about 2 and about 15.

The aforementioned conditions of temperature and pressure are generally applicable over their entire range when the zeolite catalyst employed does not possess hydrogenation/dehydrogenation activity.

When hydrogenation/dehydrogenation activity is associated with the zeolite catalyst, greater care must be taken in choosing conditions of temperature and pressure so that aromatics present in the reformate or reformer effluent are not hydrogenated.

What is claimed is:

1. In a process for increasing the aromatic content of a liquid hydrocarbon charge comprising paraffins and cycloparaffins by contact with a solid catalyst under conversion temperatures of at least 180° C. and recovering from such conversion a liquid hydrocarbon product of greater aromatic content than said charge; the improvement consisting of conducting such conversion by contacting said charge with a catalyst comprising a crystalline aluminosilicate zeolite characterized by a silica to alumina ratio of at least 10.

2. A process according to claim 1 wherein a petroleum naphtha is catalytically reformed.

3. A process for the alkylation of an aromatic hydrocarbon which comprises contacting said aromatic hydrocarbon with an alkylating agent in an alkylation reaction zone under alkylation conditions with a catalyst consisting essentially of a crystalline aluminosilicate zeolite having a silica to alumina ratio of at least 10.

4. The process of claim 1 wherein the aluminosilicate has been base exchanged with ammonium or hydrogen ions.

5. The process of claim 1 wherein the aluminosilicate is at least 50 percent in the hydrogen form.

6. The process of claim 3 wherein said aromatic hydrocarbon is benzene.

7. The process of claim 3 wherein said alkylating agent is an olefin.

8. The process of claim 7 wherein said olefin is ethylene.

9. The process of claim 7 wherein said olefin is propylene.

* * * * *

UNITED STATES PATENT AND TRADEMARK OFFICE
CERTIFICATE OF CORRECTION

PATENT NO. : 4,157,950

DATED : June 12, 1979

INVENTOR(S) : Vincent J. Frilette and Mae K. Rubin

It is certified that error appears in the above-identified patent and that said Letters Patent are hereby corrected as shown below:

| | | |
|---|---|---|
| Column 1 | Line 9 | Delete "filed Aug. 3, 1971,". |
| Column 1 | Formula | Delete the "1" at the end of the formula. |
| Column 2 | Line 34 | "(465°E)" should read --(465°F)--. |
| Column 6 | Line 39 | "M1/n0" should read --M2/n0--. |

Signed and Sealed this

Twentieth Day of November 1979

[SEAL]

Attest:

RUTH C. MASON
*Attesting Officer*

LUTRELLE F. PARKER
*Acting Commissioner of Patents and Trademarks*